United States Patent
Berry et al.

(12)

(10) Patent No.: US 6,277,806 B1
(45) Date of Patent: Aug. 21, 2001

(54) BLEACHING ENZYMES AND DETERGENT COMPOSITIONS COMPRISING THEM

(75) Inventors: Mark John Berry, Sharnbrook (GB); Daniel Convents, Vlaardingen (NL); Paul James Davis, Sharnbrook (GB); Michael John Gidley, Sharnbrook (GB); Cornelis Paul Van Der Logt, Sharnbrook (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/456,805

(22) Filed: Dec. 8, 1999

(30) Foreign Application Priority Data

Dec. 11, 1998 (EP) .................................................. 98310204

(51) Int. Cl.[7] ............................... C11D 1/00; C11D 3/16; C11D 3/395
(52) U.S. Cl. ......................... 510/392; 510/320; 510/321; 510/226; 510/393; 510/305; 510/374
(58) Field of Search .................................... 510/320, 321, 510/226, 592, 392, 393, 305, 309, 310, 311, 374; 8/137

(56) References Cited

U.S. PATENT DOCUMENTS

| | | | |
|---|---|---|---|
| 4,421,668 | 12/1983 | Cox et al. | 252/174.12 |
| 5,273,896 | * 12/1993 | Pedersen et al. | 435/192 |
| 6,171,345 | * 1/2001 | Convents et al. | 8/137 |

FOREIGN PATENT DOCUMENTS

| | | |
|---|---|---|
| 0 736 544 | 10/1996 | (EP) . |
| 89/09813 | 10/1989 | (WO) . |
| 91/00108 | 1/1991 | (WO) . |
| 91/00112 | 1/1991 | (WO) . |
| WO 91/06574 | * 5/1991 | (WO) . |
| 94/25591 | * 11/1994 | (WO) . |
| 95/07972 | * 3/1995 | (WO) . |
| 0736544 | * 10/1996 | (WO) . |
| 97/04102 | * 2/1997 | (WO) . |
| 97/14719 | 4/1997 | (WO) . |
| 97/38102 | 10/1997 | (WO) . |
| 97/40127 | 10/1997 | (WO) . |
| 98/56885 | 12/1998 | (WO) . |

OTHER PUBLICATIONS

Patent Abstract of Japan, JP 07285999, Oct. 31, 1995.

Vandenbosch, K.A. et al., Common Components of the Infection Thread Matrix and the Intercellular Space Identified by Immunocytochemical Analysis of Pea Nodules and Uninfected Roots, The EMBO Journal, vol. 8, No. 2, pp. 335–342, 1989.

PCT Search Report in an International Patent Application, PCT/EP 99/09179.

* cited by examiner

*Primary Examiner*—Gregory Delcotto
(74) *Attorney, Agent, or Firm*—Rimma Mitelman

(57) ABSTRACT

There is provided a bleaching enzyme capable of generating a bleaching chemical and having a high binding affinity for non-colored compounds present in stains on fabrics, said non-colored compounds having a molecular weight of at least 100, preferably of at least 1,000 and more preferably of at least 5,000. Furthermore, there is provided an enzymatic bleaching composition comprising said bleaching enzyme and a surfactant and a process for bleaching stains present of fabrics.

10 Claims, No Drawings

BLEACHING ENZYMES AND DETERGENT COMPOSITIONS COMPRISING THEM

TECHNICAL FIELD

The present invention generally relates to bleaching enzymes. More in particular, it relates to bleaching enzymes capable of generating a bleaching chemical and having a high binding affinity for non-coloured compounds present in stains on fabrics. The invention also relates to a detergent composition comprising said enzymes and to a process for bleaching stains present on fabrics.

BACKGROUND AND PRIOR ART

Detergent compositions comprising bleaching enzymes have been described in the prior art. For instance, GB-A-2 101 167 (Unilever) discloses an enzymatic bleach composition in the form of a hydrogen peroxide-generating system comprising $C_1$–$C_4$ alkanol oxidase and a $C_1$–$C_4$ alkanol. Such enzymatic bleach compositions may be used in detergent compositions for fabric washing, in which they may provide a low-temperature enzymatic bleach system. In the wash liquor, the alkanol oxidase enzyme catalyses the reaction between dissolved molecular oxygen and the alkanol to form an aldehyde and hydrogen peroxide. In order to obtain a significant bleach effect at low wash temperatures, e.g. at 15–55° C., the hydrogen peroxide must be activated by means of a bleach activator. Today, the most commonly used bleach activator is tetra-acetyl ethylene diamine (TAED), which yields peracetic acid upon reacting with the hydrogen peroxide, the peracetic acid being the actual bleaching agent.

Although this and several other enzymatic bleach systems have been proposed, there is still a need for alternative or improved enzymatic bleach systems. In particular, the enzymatic bleach system should be capable of bleaching stains which are otherwise difficult to remove, the so-called "problem stains" such as tomato, tea, blackberry juice, or red wine. Such stains would require a significant amount of bleaching for their removal, which might negatively affect the colours of the garment.

In conventional laundry bleach systems, fabrics are uniformly exposed to the same concentration of bleach, whether "problem stains" are present or not. Moreover, repeated washing with conventional bleach systems, which may contain relatively high concentrations of bleach, may cause damage to garments such as the fading of dyes.

It is therefore an object of the present invention to provide alternative or improved enzymatic bleach systems which, in particular, should be capable of bleaching stains which are otherwise difficult to remove, and should preferably be more selective in its bleaching action. It is a further object of the present invention to provide an alternative or improved enzymatic process for bleaching stains on fabrics.

We have now surprisingly found that it is possible to control the bleaching reaction in an enzymatic bleach process by using the bleaching enzyme according to the invention, which is capable of generating a bleaching chemical and has a high binding affinity for non-coloured compounds present in stains on fabrics, said non-coloured compounds having a molecular weight of at least 100, preferably at least 1,000. Even more preferably, the non-coloured compounds have a molecular weight of at least 5,000 and especially preferred are compounds having a molecular weight of at least 10,000. Preferably, the enzyme comprises an enzyme part capable of generating a bleaching chemical, coupled to a reagent having a high binding affinity for the non-coloured compounds present in stains on fabrics.

The new bleaching enzyme is particularly attractive for treating "problem stains" which occur only occasionally, such as fruits and vegetables. These stains are not present on most garments and when they are present they are likely to be present in different positions than habitual stains such as those found on collars and cuffs. According to the invention, it is possible to optimise the in-use concentration of the new bleaching enzyme so that threshold concentrations of bleach are only reached if stain is present and the new bleaching enzyme binds to and accumulates on said stain. When this happens, the high local concentration of enzyme generates a high local concentration of bleach near to the stain and thereby exerts a selective bleaching action where it is required. Therefore, the unstained part of the garment (typically the majority) is not exposed to high levels of bleach and thereby this fabric is protected from bleach-associated damage. Moreover, the next time the same garment has a stain such as fruit or vegetable stains, it is likely to be in a different position on the garment. Therefore, a different position on the garment will be exposed to high levels of bleach. Therefore, problems associated with several washes in conventional bleaching systems, such as dye-fade, will be reduced or eliminated altogether. This is in stark contrast to conventional bleaching systems where all garments are uniformly exposed to high concentrations of bleach, in every wash, regardless of whether problem stains are present or not.

DEFINITION OF THE INVENTION

According to a first aspect of the invention, there is provided a bleaching enzyme capable of generating a bleaching chemical and having a high binding affinity for non-coloured compounds present in stains on fabrics, said non-coloured compounds having a molecular weight of at least 100, preferably at least 1,000. Preferably, the enzyme comprises an enzyme part capable of generating a bleaching chemical, coupled to a reagent having a high binding affinity for the non-pigmented compounds present in stains on fabrics.

According to a second aspect, there is provided an enzymatic bleaching composition comprising one or more surfactants and the bleaching enzyme according to the invention.

According to a third aspect, there is provided a process for bleaching stains present of fabrics, wherein stained fabrics are contacted with an a solution comprising the bleaching enzyme of the invention.

DESCRIPTION OF THE INVENTION

1. The Bleaching Enzyme

In its first aspect, the invention relates to a bleaching enzyme which is capable of generating a bleaching chemical and has a high binding affinity for stains present on fabrics. Preferably, the enzyme comprises an enzyme part capable of generating a bleaching chemical which is coupled to a reagent having a high binding affinity for non-coloured compounds present in stains on fabrics. Said non-coloured compounds have a molecular weight of at least 100, preferably of at least 1,000, more preferably of at least 5,000. Especially preferred are non-coloured compounds having a molecular weight of at least 10,000.

1.1 The Enzyme Part, Capable of Generating a Bleaching Chemical

The bleaching chemical may be enzymatically generated hydrogen peroxide. The enzyme for generating the bleaching chemical or enzymatic hydrogen peroxide-generating system may in principle be chosen from the various enzymatic hydrogen peroxide-generating systems which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. Alternatively, a combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative *Hansenula polymorpha* strain. (see for example EP-A-244 920 (Unilever)). The preferred oxidases are glucose oxidase, galactose oxidase and alcohol oxidase.

A hydrogen peroxide generating enzyme could be used in combination with activators which generate peracetic acid. Such activators are well-known in the art. Examples include tetraacetylethylenediamine (TAED) and sodium nonanoyloxybenzenesulphonate (SNOBS). These and other related compounds are described in fuller detail by Grime and Clauss in Chemistry & Industry (Oct. 15, 1990) 647–653. Alternatively, a transition metal catalyst could be used in combination with a hydrogen peroxide generating enzyme to increase the bleaching power. Examples of manganese catalysts are described by Hage et al. (1994) Nature 369, 637–639.

Alternatively, the bleaching chemical is hypohalite and the enzyme part is then a haloperoxidase. Preferred haloperoxidases are chloroperoxidases and the corresponding bleaching chemical is hypochlorite. Especially preferred chloroperoxidases are Vanadium chloroperoxidases, for example from *Curvularia inaequalis*.

Alternatively, peroxidases or laccases may be used. In this case the bleaching molecule is derived from an enhancer molecule that has reacted with the enzyme. Examples of laccase/enhancer systems are given in WO-A-95/01426. Examples of peroxidase/enhancer systems are given in WO-A-97/11217.

1.2 The Part Having the High Binding Affinity

The new bleaching enzyme has a high binding affinity for non-coloured compounds present in stains on fabrics, said non-coloured compounds having a molecular weight of at least 100, preferably at least 1,000, more preferably of at least 5,000 Daltons. It will be understood that the non-coloured compounds may also have higher molecular weights of at least 10,000, 100,000 or even 1,000,000 Daltons or more. It may be that one part of the polypeptide chain of the bleaching enzyme is responsible for the binding affinity, but it is also possible that the enzyme comprises an enzyme part capable of generating a bleaching chemical which is coupled to a reagent having the high binding affinity for the non-coloured compounds present in stains on fabrics. In the first situation, the bleaching enzyme may be a fusion protein comprising two domains which may be coupled by means of a linker. In the second situation, the reagent having the high binding affinity may be covalently coupled to the enzyme part for generating the bleaching chemical, by means of a bi-valent coupling agent such as glutardialdehyde. A full review of chemistries appropriate for coupling two biomolecules is provided in "Bioconjugate techniques" by Greg T. Hermanson, Academic Press Inc (1986). Alternatively, if the reagent having the high binding affinity is a peptide or a protein, it may also be coupled to the enzyme by constructing a fusion protein. In such a construct there would typically be a peptide linker between the binding reagent and the enzyme. An example of a fusion of an enzyme and a binding reagent is described in Ducancel et al. Bio/technology 11, 601–605.

A further embodiment would be for the reagent with a high binding affinity to be a bispecific reagent, comprising one specificity for non-coloured compounds present in stains on fabrics, said non-coloured compounds having a molecular weight of at least 1,000, preferably of at least 5,000 and more preferably of at least 10,000. Such a reagent could fulfil the requirement of accumulating enzyme on the stain either by supplying said reagent together with enzyme as a pre-formed non-covalent complex or by supplying the two separately and allowing them to self-assemble either in the wash liquor or on the stain.

The novel bleaching enzyme according to the invention is based on the presence of a part having a high binding affinity for non-coloured compounds present in stains on fabrics, said non-coloured compounds having a molecular weight of at least 100, preferably of at least 1,000 and more preferably of at least 5,000.

The degree of binding of a molecule A to another molecule B can be generally expressed by the chemical equilibrium constant $K_d$ resulting from the following reaction:

$$[A]+[B] \Longleftrightarrow [A \equiv B]$$

The chemical equilibrium constant $K_d$ is then given by:

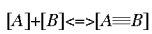

$$K_d = \frac{[A] \times [B]}{[A \equiv B]}$$

Whether the binding of a molecule to a non-coloured compound present in stains on fabrics is specific or not can be judged from the difference between the binding ($K_d$ value) of the molecule to stained (i.e. a material treated so that stain components are bound on), versus the binding to unstained (i.e. untreated) material. For applications in laundry, said material will be a fabric such as cotton or polyester. However, it will usually be more convenient to measure $K_d$ values and differences in $K_d$ values on other materials such as a polystyrene microtitre plate or a specialised surface in an analytical biosensor. The difference between the two binding constants should be minimally 10, preferably more than 100, and more preferably, more that 1000. Typically, the compound should bind the stain, or the stained material, with a $K_d$ lower than $10^{-4}$ M, preferably lower than $10^{-6}$ M and could be $10^{-10}$ M or even less. Higher binding affinities ($K_d$ of less than $10^{-5}$ M) and/or a larger difference between the non-coloured substance and background binding would increase the selectivity of the bleaching process. Also, the weight efficiency of the molecule in the total detergent composition would be increased and smaller amounts of the molecule would be required.

Several classes of molecules can be envisaged which deliver the capability of specific binding to non-coloured compounds present in stains one would like to bleach. In the following we will give a number of examples of such molecules having such capabilities, without pretending to be exhaustive.

1.2.1. Antibodies

Antibodies are well known examples of molecules which are capable of binding specifically to compounds against which they were raised. Antibodies can be derived from several sources. From mice, monoclonal antibodies can be obtained which possess very high binding affinities. From such antibodies, Fab, Fv or scFv fragments, can be prepared which have retained their binding properties. Such antibodies or fragments can be produced through recombinant DNA technology by microbial fermentation. Well known production hosts for antibodies and their fragments are yeast, moulds or bacteria.

A class of antibodies of particular interest is formed by the Heavy Chain antibodies as found in Camelidae, like the camel or the llama. The binding domains of these antibodies consist of a single polypeptide fragment, namely the variable region of the heavy chain polypeptide (HC-V). In contrast, in the classic antibodies (murine, human, etc.), the binding domain consist of two polypeptide chains (the variable regions of the heavy chain ($V_h$) and the light chain ($V_1$)). Procedures to obtain heavy chain immunoglobulins from Camelidae, or (functionalized) fragments thereof, have been described in WO-A-94/04678 (Casterman and Hamers) and WO-A-94/25591 (Unilever and Free University of Brussels).

Alternatively, binding domains can be obtained from the $V_h$ fragments of classical antibodies by a procedure termed "camelization". Hereby the classical $V_h$ fragment is transformed, by substitution of a number of amino acids, into a HC-V-like fragment, whereby its binding properties are retained. This procedure has been described by Riechmann et al. in a number of publications (J. Mol. Biol. (1996) 259, 957–969; Protein. Eng. (1996) 9, 531–537, Bio/Technology (1995) 13, 475–479). Also HC-V fragments can be produced through recombinant DNA technology in a number of microbial hosts (bacterial, yeast, mould), as described in WO-A-94/29457 (Unilever).

Methods for producing fusion proteins that comprise an enzyme and an antibody or that comprise an enzyme and an antibody fragment are already known in the art. One approach is described by Neuberger and Rabbits (EP-A-194 276). A method for producing a fusion protein comprising an enzyme and an antibody fragment that was derived from an antibody originating in Camelidae is described in WO-A-94/25591. A method for producing bispecific antibody fragments is described by Holliger et al. (1993) PNAS 90, 6444–6448.

A particularly attractive feature of antibody binding behaviour is their reported ability to bind to a "family" of structurally-related molecules. For example, in Gani et al. (J. Steroid Biochem. Molec. Biol. 48, 277–282) an antibody is described that was raised against progesterone but also binds to the structurally-related steroids, pregnanedione, pregnanolone and 6-hydroxy-progesterone. Therefore, using the same approach, antibodies could be isolated that bind to a whole "family" of stain chromophores (such as the polyphenols, porphyrins, or caretenoids as described below). A broad action antibody such as this could be used to treat several different stains when coupled to a bleaching enzyme.

1.2.2. Peptides

Peptides usually have lower binding affinities to the substances of interest than antibodies. Nevertheless, the binding properties of carefully selected or designed peptides can be sufficient to deliver the desired selectivity in a oxidation process. A peptide which is capable of binding selectively to a substance which one would like to oxidise, can for instance be obtained from a protein which is known to bind to that specific substance. An example of such a peptide would be a binding region extracted from an antibody raised against that substance. Other examples are proline-rich peptides that are known to bind to the polyphenols in wine.

Alternatively, peptides which bind to such substance can be obtained by the use of peptide combinatorial libraries. Such a library may contain up to $10^{10}$ peptides, from which the peptide with the desired binding properties can be isolated. (R. A. Houghten, Trends in Genetics, Vol 9, no &, 235–239).

Several embodiments have been described for this procedure (J. Scott et al., Science (1990) 249, 386–390; Fodor et al., Science (1991) 251, 767–773; K. Lam et al., Nature (1991) 354, 82–84; R. A. Houghten et al., Nature (1991) 354, 84–86).

Suitable peptides can be produced by organic synthesis, using for example the Merrifield procedure (Merrifield (1963) J.Am.Chem.Soc. 85, 2149–2154). Alternatively, the peptides can be produced by recombinant DNA technology in microbial hosts (yeast, moulds, bacteria)(K. N. Faber et al. (1996) Appl. Microbiol. Biotechnol. 45, 72–79).

1.2.3. Pepidomimics

In order to improve the stability and/or binding properties of a peptide, the molecule can be modified by the incorporation of non-natural amino acids and/or non-natural chemical linkages between the amino acids. Such molecules are called peptidomimics (H. U. Saragovi et al. (1991) Bio/Technology 10, 773–778; S. Chen et al. (1992) Proc.Nat-l.Acad. Sci. USA 89, 5872–5876). The production of such compounds is restricted to chemical synthesis.

1.2.4. Other Organic Molecules

It can be readily envisaged that other molecular structures, which need not be related to proteins, peptides or derivatives thereof, can be found which bind selectively to substances one would like to oxidise with the desired binding properties. For example, certain polymeric RNA molecules which have been shown to bind small synthetic dye molecules (A. Ellington et al. (1990) Nature 346, 818–822). Such binding compounds can be obtained by the combinatorial approach, as described for peptides (L. B. McGown et al. (1995), Analytical Chemistry, 663A–668A).

This approach can also be applied for purely organic compounds which are not polymeric. Combinatorial procedures for synthesis and selection for the desired binding properties have been described for such compounds (Weber et al. (1995) Angew.Chem.Int.Ed.Engl. 34, 2280–2282; G. Lowe (1995), Chemical Society Reviews 24, 309–317; L. A. Thompson et al. (1996) Chem. Rev. 96, 550–600). Once suitable binding compounds have been identified, they can be produced on a larger scale by means of organic synthesis.

1.3 The Non-coloured Compounds Present in Stains on Fabrics

For laundry detergent applications, several classes of coloured substances one would like to bleach can be envisaged, in particular coloured substances which may occur as stains on fabrics can be a target. It was found to be advantageous to target the bleaching enzymes not directly to such coloured stains themselves, but rather to macromolecular compounds which themselves are not coloured but which are associated with the stains. Such macromolecular compounds have the advantage that they can have a more immunogenic nature, i.e. that it is easier to raise antibodies against them. Furthermore, they are more accessible at the surface of the stains than coloured substances, which generally have a low molecular weight. Finally, it is important to emphasise that although many stains are heterogeneous, certain non-coloured compounds are commonly present in a variety of stains.

It the context of the present invention, a non-coloured compound is defined as a compound which, in purified form in solution and after correcting for effects such as the scattering of light, has an optical density (or adsorption) for all wavelengths in the visible spectrum (i.e. from 325 nm to 900 nm) and for a light path of 1 cm at a concentration of 1 mg/ml in solution of less than 0.2 and preferably less than 0.05.

An important embodiment of the invention is to use a binding molecule (as described above) that binds to several different, but structurally-related, non-coloured molecules in a class of "stain substances". This would have the advantage of enabling a single enzyme species to bind (and bleach) several different stains. Some examples of classes of non-coloured compounds associated with stains are given below:

1.3.1. Pectins

Pectins are a heterogeneous group of polysaccharides which are rich in D-galacturonic acid. They are one of the most important components in the cell wall matrix of plant cells. For a review see A. Jauneau et al. (1998) Int. J. Plant Sci. 159 (1) 1–13.

1.3.2. Beta-lactoglobulin

Beta-lactoglobulin (BLG) is the major whey protein in the milk of various species including cows, sheep, goats, horses, and pigs. For a review see J. Godovac-Zimmermann and G. Braunitzer (1987) Milchwissenschaft 42 (5) 294–297.

2. The Detergent Composition

The bleaching enzymes of the invention can be used in a laundry detergent composition which is specifically suited for stain bleaching purposes, and this constitutes a second aspect of the invention. To that extent, the composition comprises one or more surfactants and optionally other conventional detergent ingredients. The invention in its second aspect provides an enzymatic detergent composition which comprises from 0.1–50% by weight, based on the total detergent composition, of one or more surfactants. This surfactant system may in turn comprise 0–95% by weight of one or more anionic surfactants and 5–100% by weight of one or more nonionic surfactants. The surfactant system may additionally contain amphoteric or zwitterionic detergent compounds, but this in not normally desired owing to their relatively high cost. It was found to be advantageous to also include cationic surfactants into the composition. Examples of suitable cationic surfactants are given in WO-A-97/03160 and WO-A-98/17767 (Procter&Gamble).

In general, the nonionic and anionic surfactants of the surfactant system may be chosen from the surfactants described "Surface Active Agents" Vol. 1, by Schwartz & Perry, Interscience 1949, Vol. 2 by Schwartz, Perry & Berch, Interscience 1958, in the current edition of "McCutcheon's Emulsifiers and Detergents" published by Manufacturing Confectioners Company or in "Tenside-Taschenbuch", H. Stache, 2nd Edn., Carl Hauser Verlag, 1981.

Suitable nonionic detergent compounds which may be used include, in particular, the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are $C_6$–$C_{22}$ alkyl phenol-ethylene oxide condensates, generally 5 to 25 EO, i.e. 5 to 25 units of ethylene oxide per molecule, and the condensation products of aliphatic $C_8$–$C_{18}$ primary or secondary linear or branched alcohols with ethylene oxide, generally 5 to 40 EO.

Suitable anionic detergent compounds which may be used are usually water-soluble alkali metal salts of organic sulphates and sulphonates having alkyl radicals containing from about 8 to about 22 carbon atoms, the term alkyl being used to include the alkyl portion of higher acyl radicals. Examples of suitable synthetic anionic detergent compounds are sodium and potassium alkyl sulphates, especially those obtained by sulphating higher $C_8$–$C_{18}$ alcohols, produced for example from tallow or coconut oil, sodium and potassium alkyl $C_9$–$C_{20}$ benzene sulphonates, particularly sodium linear secondary alkyl $C_{10}$–$C_{15}$ benzene sulphonates; and sodium alkyl glyceryl ether sulphates, especially those ethers of the higher alcohols derived from tallow or coconut oil and synthetic alcohols derived from petroleum. The preferred anionic detergent compounds are sodium $C_{11}$–$C_{15}$ alkyl benzene sulphonates and sodium $C_{12}$–$C_{18}$ alkyl sulphates. Also applicable are surfactants such as those described in EP-A-328 177 (Unilever), which show resistance to salting-out, the alkyl polyglycoside surfactants described in EP-A-070 074, and alkyl monoglycosides.

Preferred surfactant systems are mixtures of anionic with nonionic detergent active materials, in particular the groups and examples of anionic and nonionic surfactants pointed out in EP-A-346 995 (Unilever). Especially preferred is surfactant system which is a mixture of an alkali metal salt of a $C_{16}$–$C_{18}$ primary alcohol sulphate together with a $C_{12}$–$C_{15}$ primary alcohol 3–7 EO ethoxylate.

The nonionic detergent is preferably present in amounts greater than 10%, e.g. 25–90% by weight of the surfactant system. Anionic surfactants can be present for example in amounts in the range from about 5% to about 40% by weight of the surfactant system.

The detergent composition may take any suitable physical form, such as a powder, a tablet, an aqueous or non aqueous liquid, a paste or a gel. The enzymatic bleaching detergent composition according to the invention will generally be used as a dilution in water of about 0.05 to 2%.

The bleaching enzyme used in the present invention can usefully be added to the detergent composition in any suitable form, i.e. the form of a granular composition, a liquid or a slurry of the enzyme, or with carrier material (e.g. as in EP-A-258 068 and the Savinase (TM) and Lipolase (TM) products of Novo Nordisk). A good way of adding the enzyme to a liquid detergent product is in the form of a slurry containing 0.5 to 50% by weight of the enzyme in a ethoxylated alcohol nonionic surfactant, such as described in EP-A-450 702 (Unilever).

The enzymatic bleaching compositions of the invention comprise about 0.001 to 10 milligrams of active bleaching enzyme per litre. A detergent composition will comprise about 0.001% to 1% of active enzyme (w/w).

The enzyme activity can be expressed in units. For example, in the case of glucose oxidase, one unit will oxidise 1 $\mu$mole of $\beta$-D-glucose to D-gluconolactone and $H_2O_2$ per minute at pH 6.5 at 30° C. The enzyme activity which is added to the enzymatic bleaching composition will be about 2.0 to 4,000 units per litre (of wash liquor).

The invention will now be further illustrated in the following, non-limiting Examples. In the examples, two types of analytical experiment are described. The first type of experiment (as described in examples 1,2 and 5) involves using a surface that is specially designed to investigate antibody binding: the microtitre plate. These experiments investigate whether the non-coloured components of stains, such as pectin in fruit and vegetables or beta-lactoglobulin in milky beverages, can be specifically targeted by antibodies in the presence of other components of the stain. In these experiments, the staining material was sometimes diluted many-fold so as to optimise antibody binding specificity. This is standard practise when working with microtitre plate assays as the technique is so sensitive and works best when using small amounts of sample. Furthermore, as the surface of the microtitre plate has been specially designed to adsorb biological material and to have very low non-specific binding effects, these experiments are the best check on antibody specificity.

In the second type of analytical experiment (as described in examples 4 and 6), swatches of cotton are stained with staining material such as tomato ketchup or milky tea under conditions that are likely to be encountered with "real" stains i.e. undiluted staining material. These experiments investigate whether the non-coloured components are accessible to antibody when bound to the porous structure of the cotton and also whether the non-coloured components remain bound to the cotton after soaking the cotton in surfactant. In contrast to coloured components, it is not possible to tell whether the non-coloured molecules are bound to the cotton simply by visual inspection. Therefore, a specific binding probe (such as an antibody) is needed to determine whether they are present. Unlike the microtitre plates, the cotton has not been specially designed for immunoassay and so it can be expected that background signal will be higher. However, the analysis of the exposure of stain marker molecules on cotton is nevertheless of critical importance to applications in laundry products.

Taking the results of both types of experiment together we have found (in our view surprisingly) that some non-coloured components of common stains are readily adsorbed onto surfaces and can be specifically targeted by antibodies even after extensive washing and soaking in surfactant. Moreover, the two experimental approaches described here could be used to define other non-coloured marker molecules in stains that could be used for the invention by virtue of being a) accessible for binding by antibody b) able to remain attached to surfaces in the presence of surfactant.

Finally, having established that a particular marker molecule is accessible and remains attached to cotton in the presence of surfactant, it is then possible to evaluate the effect of treating a stain with an antibody/oxidase conjugate that has a specific binding affinity for said marker molecule. Such an experiment is described in example 8.

EXAMPLE 1
Binding of a Pectin-specific Antibody to a Microtitre Plate Sensitised With Tomato Products A rat monoclonal antibody that is specific for pectin and known as "JIM5" (K. A. VandenBosch et al. EMBO Journal vol. 8 no. 2 pp.335–342, 1989; J. P. Knox et al. Planta (1990) 181: 512–521) was used. However, other antibodies that bind pectin could also be used. Methods of how to raise such antibodies by inoculation are known. See for instance K. A. VandenBosch et al. as above and F. Liners et al. Plant Physiol. (1989) 91, 1419–1424. The antibody preparation used in this example was a culture supernatant that was a gift from the John Innes Centre, Norwich, U.K.

Tomato ketchup (H. J. Heinz Co Ltd. Hayes, U.K.) and sieved tomatoes (Valfrutta) were diluted approximately 1,000-fold in phosphate buffered saline, PBS [0.01M $Na_2HPO_4/NaH_2PO_4$, 0.15M NaCl (pH 7)]. The diluted tomato samples were applied to the wells of microtitre plates (high capacity, flat-bottomed ELISA plates; Greiner Labortechnik) and incubated at 37° C. for 48 hours with an air-tight plastic seal. As a negative control, some wells were treated with PBS only.

The sensitised plates were washed with PBST [PBS+ 0.15% tween 20 (Sigma)] using an automated microtitre plate washer. Then a range of dilutions of the JIM5 preparation (dilutions were made in PBST) were applied to the wells and incubated for 1 hour at room temperature. Control wells were treated with either a negative culture supernatant (not containing JIM 5) or PBST only.

Plates were washed as above and then a Sheep anti-rat IgG/alkaline phosphatase conjugate (Serotec Product No AAR02A) was applied to the wells. The conjugate was diluted 1 in 1,000 in PBST and incubated in the wells for 1 hour at room temperature.

The plates were washed as above and then substrate buffer was applied. [1 mg/ml para-nitrophenyl phosphate (pNPP) in 1M diethylamine (pH 9.8); 1 mM $MgCl_2$]. Signal was read at 405 nm in an automated plate reader after 5 minutes.

The results are given below in Table 1 as optical densities or "signal" recorded at 405 nm—the higher the signal, the more antibody has bound to the surface.

TABLE 1

| | Antibody reagent applied | | | | |
|---|---|---|---|---|---|
| Sensitisation | JIM5/10 | JIM5/100 | JIM5/1,000 | None | NC/10 |
| Sieved tomatoes | 1.2 | 0.89 | 0.16 | 0.01 | 0.01 |
| Tomato ketchup | 0.98 | 0.71 | 0.15 | 0.00 | 0.00 |
| None | 0.01 | 0.01 | 0.01 | 0.01 | 0.01 |

JIM5/10=JIM5 culture diluted 1 in 10 in PBST
JIM5/100=JIM5 culture diluted 1 in 100 in PBST
JIM5/1,1000=JIM5 culture diluted 1,1000 in PBST
NC/10=Negative culture diluted 1 in 10 in PBST The results show that JIM5 can specifically bind to both tomato products when adsorbed onto the microtitre plate. Therefore, it is concluded that pectin remains bound to the surface in an accessible form even after washing the surface with a surfactant-containing liquid (PBST).

EXAMPLE 2
Binding of a Pectin-specific Antibody to a Microtitre Plate Sensitised With Orange Juice Pure, unsweetened orange juice (Safeway) was diluted approximately 1,000-fold in phosphate buffered saline, PBS [0.01M $Na_2HPO_4/NaH_2PO_4$, 0.15M NaCl (pH 7)]. The diluted orange sample was applied to the wells of microtitre plates (Greiner, high capacity) and incubated at 37° C. overnight with an air-tight plastic seal. As a negative control, some wells were treated with PBS only.

The sensitised plates were washed with PBST [PBS+ 0.15% tween 20 (Sigma)] using an automated microtitre plate washer. Then a range of dilutions of the JIM5 preparation (dilutions were made in PBST) were applied to the wells and incubated for 1.5 hours at room temperature. Control wells were treated with either a negative culture supernatant (not containing JIM 5), a non-specific rat monoclonal antibody (Serotec product PRP04) made up to 4 µg/ml in PBST, or PBST only.

Plates were washed as above and then a Sheep anti-rat IgG/alkaline phosphatase conjugate (Serotec Product No AAR02A) was applied to the wells. The conjugate was diluted 1 in 1,000 in PBST and incubated in the wells for 1 hour at room temperature. The plates were washed as above and then substrate buffer was applied. (1 mg/ml pNPP in 1M diethylamine (pH 9.8); 1 mM $MgCl_2$). Signal was read at 405 nm in an automated plate reader after 40 minutes.

The results are given in Tables 2 and 3 below as optical densities or "signal" recorded at 405 nm—the higher the signal, the more antibody has bound to the surface.

TABLE 2

| | Antibody reagent applied | | | |
|---|---|---|---|---|
| Sensitisation | JIM5/10 | JIM5/40 | JIM5/160 | JIM5/640 |
| Orange juice | 1.37 | 0.63 | 0.17 | 0.05 |
| None | 0.06 | 0.06 | 0.07 | 0.07 |

JIM5/10=JIM5 culture diluted 1 in 10 in PBST
JIM5/40=JIM5 culture diluted 1 in 40 in PBST
JIM5/160=JIM5 culture diluted 1 in 160 in PBST
JIM5/640=JIM5 culture diluted 1 in 640 in PBST

TABLE 3

| | Negative control applied | | |
|---|---|---|---|
| Sensitisation | None | NC/10 | NAb |
| Orange juice | 0.02 | 0.02 | 0.03 |
| None | 0.07 | 0.07 | 0.08 |

None=PBST only
NC/10=Negative culture diluted 1 in 10 in PBST
NAb=Non-specific rat monoclonal antibody at 4 µg/ml in PBST.

EXAMPLE 3
Purification of JIM5 from Culture Supernatant 500 ml of clarified culture was concentrated to approximately 12 ml using a stirred cell (Amicon) fitted with an ultrafiltration membrane (Amicon PM30). The concentrate was applied to a Protein G "Hi-Trap" column (Pharmacia). The column was then washed with PBS to remove non-specifically bound material. JIM5 antibody was then specifically eluted by washing the column with 0.1M glycine buffer (pH 2.5). The desorbed fraction was immediately neutralised with 1/20 volume 3M tris (pH 8.8). The neutralized fraction was dialysed into PBS. Recovered antibody was determined by measuring the absorbance at 280 nm, assuming an extinction coefficient of 1.4 for a concentration of 1 mg/ml protein.

EXAMPLE 4
Binding of Purified Pectin-specific Antibody to Cotton Swatches Stained With Tomato Eighteen 1 cm×1 cm cotton swatches were cut from white de-sized cotton fabric and labelled with a "B" pencil so that they could be identified. Six swatches were stained by submerging them in tomato ketchup (Heinz) and incubated at 37° C. overnight in a sealed Petri dish. Six were stained by submerging in sieved tomatoes (Valfrutta) and incubated at 37° C. overnight in a sealed tube. Six were not stained.

The stained swatches were pre-washed so that the stains became typical of those described as "residual" i.e. faint but stubborn. Swatches were pre-washed in batches of six, according to stain type, so that cross-contamination of stain material between different batches was minimised. They were rinsed with distilled water to remove surplus tomato and then washed vigorously in 3×100 ml of wash buffer (PBS+0.2% Co—Co 6.5EO). They were recovered from each wash with a tea strainer. After the third wash, they were blot-dried on paper towel.

Swatches were then placed in plastic tubes containing 2 ml of antibody at 5 µg/ml in wash buffer. Antibody was either purified JIM5 (as described in example 3) or a non-specific rat monoclonal antibody of the same sub-class (Serotec Product number PRP04). Each type of swatch was kept separate according to stain type to minimise cross-contamination. There were therefore a total of six tubes, each tube contained three swatches, every swatch in a single tube had undergone the same treatment, as summarised in Table 4 below.

TABLE 4

| Tube | Antibody | Stain |
|---|---|---|
| 1 | JIM5 | Ketchup |
| 2 | JIM5 | Sieved tomatoes |

TABLE 4-continued

| Tube | Antibody | Stain |
|---|---|---|
| 3 | JIM5 | None |
| 4 | Non-specific | Ketchup |
| 5 | Non-specific | Sieved tomatoes |
| 6 | Non-specific | None |

Tubes were incubated for 2 hours at room temperature. Then they were washed with 3×100 ml of wash buffer, blotted dry and then placed in conjugate. The conjugate was a sheep anti-ratIgG/alkaline phosphatase conjugate (Serotec product number AAR02A) diluted 1 in 1,000 in wash buffer. The tubes were incubated for a further 2 hours at room temperature. Again, stained and un-stained swatches were kept apart to minimise cross-contamination of stain material.

Swatches were washed and dried as before and then individually placed in 1 ml of substrate buffer [1 mg/ml pNPP in 1M diethylamine (pH 9.8); 1 mM $MgCl_2$)]. The substrate was dispensed into the wells of a 24-well cell culture plate (Costar, Cambridge USA) and the swatches were incubated for 30 minutes at room temperature, before removing 200 µl for reading in a microtitre plate reader.

Results are given in Table 5 below as optical densities or "signal" recorded at 405 nm—the higher the signal, the more antibody has bound to the cotton. Results are given for replicate swatches and then mean figures have been calculated.

TABLE 5

| Antibody | Stain | Signal (A405) | Mean signal |
|---|---|---|---|
| JIM5 | Ketchup | 1.185, 0.942, 1.214 | 1.1 |
| JIM5 | Sieved tomatoes | 1.048, 1.052, 0.947 | 1.0 |
| JIM5 | None | 0.494, 0.581, 0.539 | 0.54 |
| non-specific | Ketchup | 0.427, 0.394, 0.348 | 0.39 |
| non-specific | Sieved tomatoes | 0.425, 0.429, 0.354 | 0.40 |
| non-specific | None | 0.527, 0.463, 0.442 | 0.47 |

The results show that the pectin-specific antibody binds to tomato-stained swatches significantly better than to unstained swatches. Therefore, it can be concluded that pectin has bound to the cotton during the staining procedure and that a significant amount remains bound even after several washes in surfactant-containing buffer. Furthermore, the pectin must be accessible to antibody even when it is bound to or within the porous structure of the cotton.

EXAMPLE 5
Binding of Lactoglobulin-specific Antibody to a Microtitre Plate Sensitised With Milky Tea A rabbit polyclonal reagent was used. This was prepared by inoculating a rabbit with beta-lactoglobulin B, or "BLG" (Sigma Product number L8005), recovering immune sera, and purifying lactoglobulin-specific antibodies by antigen affinity chromatography. Methods describing how to do this are published by S. C. Williams et al. [J. Immunological Methods 213 (1998) 1–17].

Tea was made by pouring boiling water onto a tea-bag (Typhoo) and then adding milk (Co-op half-fat milk). The tea was allowed to cool and then applied to the wells of a microtitre plate (Greiner, high capacity) and then incubated at 37° C. for 48 hours with an air-tight seal.

The sensitised plates were washed with PBST (PBS+ 0.15% tween 20) using an automated microtitre plate washer. Then a range of dilutions of the lactoglobulin-specific antibody (dilutions were made in PBST) were applied to the wells and incubated for 2 hours at room temperature. Control wells were treated with a non-specific rabbit antibody i.e. a antibody that had been raised against a different antigen (Dako rabbit anti-mouse, product number Z259, Dako A/S, Glostrup, Denmark). Other control wells were treated with PBST only.

Plates were washed as above and then a goat anti-rabbit IgG/alkaline phosphatase conjugate (Zymed Laboratories Inc, San Fransisco, Product No 62-6122) was applied to the wells. The conjugate was diluted 1 in 1,000 in PBST and incubated in the wells for 1 hour at room temperature. The plates were washed as above and then substrate buffer was applied (1 mg/ml pNPP in 1M diethylamine (pH 9.8); 1 mM $MgCl_2$). Signal was read at 405 nm in an automated plate reader after 30 minutes. The results are given in Table 6 below as optical densities or "signal" recorded at 405 nm—the higher the signal, the more antibody has bound to the surface.

TABLE 6

| Sensitisation | Antibody reagent applied | | | | | |
| --- | --- | --- | --- | --- | --- | --- |
| | anti-BLG at 4 µg/ml | anti-BLG at 1 µg/ml | Anti-BLG At 250 ng/ml | anti-BLG at 62 ng/ml | none | NAb at 4 µg/ml |
| Milky Tea | 2.12 | 1.09 | 0.28 | 0.07 | 0.01 | 0.06 | anti-BLG = Rabbit anti-lactoglobulin
NAb = Non-specific rabbit antibody
None = PBST only The results show that the anti-lactoglobulin antibody can bind lactoglobulin (both specifically and in a dose-dependant manner) when adsorbed onto a surface in the presence of tea.

EXAMPLE 6

Binding of Lactoglobulin-specific Antibody to Cotton Swatches Stained With Milky Tea Eighteen 1 cm×1 cm cotton swatches were cut from white de-sized cotton fabric and labelled with a "B" pencil so that they could be identified. Nine swatches were stained by submerging them in milky tea (made with Typhoo tea bag and Co-op half-fat milk) and incubating at 37° C. overnight in a sealed tube. Nine were not stained.

The stained swatches were pre-washed so that the stains became typical of those described as "residual" i.e. faint but stubborn. They were washed vigorously in 3×100 ml of wash buffer (PBS+0.2% Co—Co 6.5EO). They were recovered from each wash with a tea strainer. After the third wash, they were blot-dried on paper towel.

Swatches were then placed in plastic tubes containing 2 ml of antibody at 5 µg/ml in wash buffer or a negative control tube containing wash buffer only. Antibody was either rabbit anti-lactoglobulin ("anti-BLG" as described in example 5) or a non-specific rabbit antibody (Dako rabbit anti-mouse, product number Z259). Each type of swatch was kept separate according to the type of treatment it had received so as to minimise cross-contamination of reagents. There were therefore a total of six tubes, each tube contained three swatches, every swatch in a single tube had undergone the same treatment, as summarised in Table 7 below.

TABLE 7

| Tube | Stain | Antibody |
| --- | --- | --- |
| 1 | Milky tea | BLG-specific |
| 2 | Milky tea | Non-specific |
| 3 | Milky tea | None |
| 4 | None | BLG-specific |
| 5 | None | Non-specific |
| 6 | None | None |

Tubes were incubated for 1.5 hours at room temperature. Then they were washed with 3×100 ml of wash buffer, blotted dry and then placed in conjugate. The conjugate was a goat anti-rabbitIgG/alkaline phosphatase conjugate (Zymed product number 62-6122) diluted 1 in 1,000 in wash buffer. The tubes were incubated for a further 1.5 hours at room temperature. Again, stained and un-stained swatches were kept apart to minimise cross-contamination of stain material.

Swatches were washed and dried as before and then individually placed in 1 ml of substrate buffer (1 mg/ml pNPP in 1M diethylamine (pH 9.8); 1 mM $MgCl_2$). The substrate was dispensed into the wells of a 24-well cell culture plate (Costar) and the swatches were incubated for 20 minutes at room temperature, before removing 200 µl for reading in a microtitre plate reader.

Results are given as optical densities or "signal" recorded at 405 nm—the higher the signal, the more antibody has bound to the cotton. The results are given below in Table 8 for replicate swatches and then mean figures have been calculated.

TABLE 8

| Stain | Antibody | Signal (A405) | Mean signal |
| --- | --- | --- | --- |
| Milky tea | BLG-specific | 0.702, 0.560, 0.586 | 0.61 |
| Milky tea | Non-specific | 0.380, 0.288, 0.322 | 0.33 |
| Milky tea | None | 0.195, 0.165 | 0.18 |
| None | BLG-specific | 0.412, 0.298, 0.245 | 0.32 |
| None | Non-specific | 0.375, 0.412, 0.295 | 0.36 |
| None | None | 0.377, 0.257, 0.329 | 0.32 |

The results show that the lactoglobulin-specific antibody binds to cotton swatches that have been stained with milky tea significantly better than to un-stained swatches. Therefore, it can be concluded that lactoglobulin has bound to the cotton during the staining procedure and that a significant amount remains bound even after several washes in surfactant-containing buffer. Furthermore, the lactoglobulin must be accessible to antibody even when it is bound to or within the porous structure of the cotton.

EXAMPLE 7

Conjugation of Pectin-specific Antibody to Glucose Oxidase Enzyme

Antibody was chemically coupled to enzyme using a protocol that was based loosely on the methods described in Carlsson et al. (1978) Biochem. J. 173, 723–737 and in "Bioconjugate Techniques" by Greg T Hermanson, Academic Press (1996), page 70–71. There are also several other methods for coupling two active proteins that are well known in The Art. The details of the precise protocols used in this example are given below.

Derivatisation of Antibody With "SAMSA"

Purified JIM5 antibody (as described in example 3) was concentrated to 6.4 mg/ml and buffer-exchanged into 0.1 M $NaH_2PO_4$, pH 6.5 by using a "Centricon 30" ultrafiltration tube (Millipore). 40 µl of this antibody preparation was dispensed into a glass reactivial. A solution of "SAMSA" [S-Acetylmercaptosuccinic anhydride (Sigma product number A-1251)] was made up. The SAMSA solution was 10 mg/ml in DMF [Dimethyl formamide]. 2 µl of the SAMSA solution was added to the antibody and the mixture stirred vigorously for 30 minutes at room temperature 21° C.±1. At the end of 30 minutes the following solutions were added at 5 minute intervals.

(i) 20 µl of EDTA to stabilise the derivatised antibody.

(ii) 100 µl of 0.1M Tris pH 7.0 to adjust the pH.

(iii) 100 µl of 1M $NH_2OH$ pH 7.0 to deprotect the SAMSA and expose thiol groups.

At 45 minutes, the mixture was made up to 2.5 ml (with 0.1 M $NaH_2PO_4$, pH 6.5) and desalted on a PD10 column (Pharamacia) previously equilibrated in 0.1 M $NaH_2PO_4$+5 mM EDTA pH 6.5. The derivatised antibody was recovered by eluting the column with 3.2 ml of buffer (in 0.1 M $NaH_2PO_4$+5 mM EDTA pH 6.5).

Derivatisation of Glucose Oxidase With "SPDP"

Glucose oxidase (or "Gox") type XS [Genencor OxyGo HPL 5000 (commercial grade)] was made up to 12.8 mg/ml in 0.1 M $NaH_2PO_4$ (pH 7.5). 62.5 ul of this enzyme preparation (0.8 mg) was placed in a reactivial with stirring, 0.5 ml of 0.1 M $NaH_2PO_4$ pH 7.5 was added. A solution of "SPDP" [3-(2-Pyridyldithio)propionic acid N-Hydroxy succinimide ester (Sigma product number P-3415)] was made up. The SPDP solution was 13.15 mg/ml in DMSO [Dimethyl sulfoxide]. 30.4 µl of the SPDP solution was added to the reactivial and the mixture was stirred for 30 minutes at room temperature. Then the mixture was made up to 2.5 ml (with 0.1 M $NaH_2PO_4$ pH 7.5) and desalted on a PD10 column (Pharamacia) previously equilibrated in 0.1 M $NaH_2PO_4$ pH 6.5. The derivatised enzyme was recovered by eluting the column with 3.2 ml of buffer (0.1 M $NaH_2PO_4$ pH 6.5).

Reaction of Derivatised Antibody With Derivatised Glucose Oxidase

The antibody and Gox preparations were pipetted into separate centricon 30 tubes (Millipore) and centrifuged at 4000 RPM until each preparation had been concentrated to a volume of about 400 µl (from a starting volume of 3.2 ml). 135 ul of the Gox preparation was mixed with all of the antibody preparation (400 µl) in a glass vial. The vial was placed at 4° C. overnight to allow conjugation to proceed.

EXAMPLE 8

Bleaching of Tomato Stain With Pectin-specific Antibody/GOx Conjugate

De-sized white cotton cloth was stained by submerging in sieved tomatoes (Valfrutta) and boiling for 1 hour. The cloth was rinsed with cold water and dried at 37° C. overnight. Dried cloth was cut into 2×2 cm square swatches and pre-rinsed "with wash buffer II" [PBS+0.0375% Coco 6.5EO, 0.0375% Las (pH 8.0)] to leave a residual stain.

6 identical swatches were added to each of 4 glass vials. Each vial was then treated with 1 ml of a different solution: vial 1 was treated with wash buffer II only; vial 2 was treated with glucose oxidase "Gox" type XS [Genencor OxyGo HPL 5000 (commercial grade)], diluted in wash buffer II; vial 3 was treated the pectin-specific antibody/Gox conjugate (as prepared in Example 7), diluted in wash buffer II; and vial 4 was treated with a non-specific antibody/Gox conjugate (comprising an antibody that does not bind pectin), again made up in wash buffer II. The enzyme preparation and the conjugates had been diluted so that they all contained an enzyme activity equivalent to approximately 2.8 µg of unconjugated Gox. The vials were incubated at room temperature for two minutes. Then 8 ml of wash buffer II was added to each vial followed by 90 µl of 1M glucose. The vials were inverted to mix the contents and placed at 37° C. for 35 minutes (Vials 2–4 now contained an enzyme activity approximately equivalent to 300 ng/ml of unconjugated Gox).

The swatches were removed and rinsed in distilled water. Each set of swatches were dried by placing in a 37° C. incubator for 3 hours. Dry cloths were analysed spectrophotometrically (using a "Color Eye 7000" spectrophotometer, Macbeth). Stain removal was expressed as $\Delta R_{440}$ and $\Delta E$, read against stained, untreated controls. The results are shown below.

TABLE 9

Removal of tomato stain with pectin-specific antibody/GOx conjugate

| Vial | R440 | $\Delta R440$ | Average $\Delta R440$ | $\Delta E$ | Average $\Delta E$ |
|---|---|---|---|---|---|
| 1. Buffer only | 63.9 | 8.2 | 8.6 | 6.1 | 6.2 |
|  | 63.4 | 7.8 |  | 5.7 |  |
|  | 63.9 | 8.3 |  | 6.2 |  |
|  | 64.8 | 9.2 |  | 6.2 |  |
|  | 65.1 | 9.4 |  | 6.7 |  |
|  | 64.5 | 8.8 |  | 6.4 |  |
| 2. Gox in buffer | 62.1 | 6.4 | 7.7 | 4.9 | 5.6 |
|  | 62.2 | 6.5 |  | 5.6 |  |
|  | 62.1 | 6.4 |  | 4.8 |  |
|  | 64.6 | 8.9 |  | 6.2 |  |
|  | 66.1 | 10.4 |  | 7.2 |  |
|  | 63.1 | 7.6 |  | 5.6 |  |
| 3. Pectin-specific antibody/Gox conjugate (in buffer) | 69.1 | 13.5 | 11.8 | 8.7 | 8.0 |
|  | 67.8 | 12.2 |  | 8.2 |  |
|  | 66.5 | 10.9 |  | 7.4 |  |
|  | 65.5 | 9.8 |  | 7.4 |  |
|  | 66.8 | 11.2 |  | 7.8 |  |
|  | 68.8 | 13.2 |  | 8.6 |  |
| 4. Non-specific antibody/GOx conjugate (in buffer) | 61.3 | 5.7 | 7.8 | 4.9 | 5.7 |
|  | 65.5 | 9.8 |  | 6.7 |  |
|  | 62.2 | 6.6 |  | 4.7 |  |
|  | 64.0 | 8.4 |  | 6.1 |  |
|  | 64.1 | 8.5 |  | 6.1 |  |
|  | 63.3 | 7.7 |  | 5.5 |  |

The results show that the pectin-specific conjugate removes more stain than the non-specific conjugate or unconjugated enzyme.

What is claimed is:

1. An enzymatic bleaching composition comprising:
    a) an enzyme capable of generating a bleaching chemical wherein the enzyme is fused to all or part of a heavy chain immunoglobulin that was raised in Camelidae and has a specificity for non-colored compounds present in stains and fabrics, said non-colored compounds having a molecular weight of at least 100;
    b) a surfactant; and
    c) an activator which generates peracetic acid.

2. An enzymatic bleaching composition comprising:
    a) an enzyme capable of generating a bleaching chemical wherein the enzyme is fused to all or part of a heavy chain immunoglobulin that was raised in Camelidae and has a specificity for non-colored compounds present in stains and fabrics, said non-colored compounds having a molecular weight of at least 100;
    b) a surfactant; and
    c) a transition metal catalyst.

3. An enzymatic bleaching composition comprising:
    a) an enzyme capable of generating a bleaching chemical wherein the enzyme is fused to all or part of a heavy chain immunoglobulin that was raised in Camelidae and has a specificity for non-coloured compounds present in stains and fabrics said non-coloured compounds having a molecular weight of at least 5,000;

b) a surfactant.

4. The composition according to claim 1, wherein the non-coloured compound is pectin or beta-lactoglobulin when the pectin or beta-lactoglobulin is adsorbed onto a fabric surface.

5. The composition according to claim 4 wherein the surface is selected from cotton, polyester, or polyester/cotton fabric.

6. The composition according to claim 1, wherein the stains are tomato stains.

7. Process for bleaching stains present on fabrics, wherein stained fabrics are contacted with a solution comprising:

a) an enzyme capable of generating a bleaching chemical wherein the enzyme is fused to all or part of a heavy chain immunoglobulin that was raised in Camelidae and has a specificity for non-colored compounds present in stains and fabrics, said non-colored compounds having a molecular weight of at least 100;

b) a surfactant.

8. The composition according to claim 1, wherein the non-coloured compounds have a molecular weight of at least 1,000.

9. The composition according to claim 1, wherein the non-coloured compounds have a molecular weight of at least 5,000.

10. The composition according to claim 1, wherein the non-coloured compounds have a molecular weight of at least 10,000.

* * * * *